US007474058B2

(12) United States Patent
Baarman (10) Patent No.: US 7,474,058 B2
(45) Date of Patent: *Jan. 6, 2009

(54) INDUCTIVELY POWERED SECONDARY ASSEMBLY

(75) Inventor: David W. Baarman, Fennville, MI (US)

(73) Assignee: Access Business Group International LLC, Ada, MI (US)

( * ) Notice: Subject to any disclaimer, the term of this patent is extended or adjusted under 35 U.S.C. 154(b) by 102 days.

This patent is subject to a terminal disclaimer.

(21) Appl. No.: 11/558,684

(22) Filed: Nov. 10, 2006

(65) Prior Publication Data

US 2007/0205730 A1    Sep. 6, 2007

Related U.S. Application Data

(60) Continuation of application No. 10/977,443, filed on Oct. 29, 2004, now Pat. No. 7,153,178, which is a continuation of application No. 10/455,694, filed on Jun. 5, 2003, now Pat. No. 6,831,417, and a continuation-in-part of application No. 09/592,194, filed on Jun. 12, 2000, now Pat. No. 6,436,299, which is a division of application No. 10/133,860, filed on Apr. 26, 2002, now Pat. No. 6,731,071.

(60) Provisional application No. 60/357,908, filed on Feb. 19, 2002, provisional application No. 60/140,159, filed on Jun. 21, 1999, provisional application No. 60/140,090, filed on Jun. 21, 1999.

(51) Int. Cl.
*H01J 13/46*    (2006.01)

(52) U.S. Cl. .............................. 315/51; 315/57; 315/58; 315/248

(58) Field of Classification Search ................... 315/46, 315/51–54, 57, 58, 62, 70, 73, 248, 276, 315/283, 344
See application file for complete search history.

(56) References Cited

U.S. PATENT DOCUMENTS

| 843,534 A | 2/1907 | Hewitt |
| 2,265,475 A | 12/1941 | Fodor |
| 3,550,682 A | 12/1970 | Fowler |
| 3,628,086 A | 12/1971 | Nuckolls |

(Continued)

FOREIGN PATENT DOCUMENTS

DE    3642890    7/1989

(Continued)

*Primary Examiner*—David H Vu
*Assistant Examiner*—Tung X Le
(74) *Attorney, Agent, or Firm*—Warner Norcross & Judd LLP (57) ABSTRACT

A lamp assembly configured to inductively receive power from a primary coil. The lamp assembly includes a lamp circuit including a secondary and a lamp connected in series. In a first aspect, the lamp circuit includes a capacitor connected in series with the lamp and the secondary to tune the circuit to resonance. The capacitor is preferably selected to have a reactance that is substantially equal to or slightly less than the reactance of the secondary and the impedance of the lamp. In a second aspect, the lamp assembly includes a sealed transparent sleeve that entirely encloses the lamp circuit so that the transparent sleeve is fully closed and unpenetrated. The transparent sleeve is preferably the lamp sleeve itself, with the secondary, capacitor and any desired starter mechanism disposed within its interior.

8 Claims, 10 Drawing Sheets

U.S. PATENT DOCUMENTS

| | | |
|---|---|---|
| 3,641,336 A | 2/1972 | Boin |
| 3,794,882 A | 2/1974 | Kitanosono |
| 3,949,268 A | 4/1976 | Von Mangoldt |
| 4,005,330 A | 1/1977 | Glascock, Jr. et al. |
| 4,017,764 A | 4/1977 | Anderson |
| 4,117,378 A | 9/1978 | Glascock, Jr. |
| 4,143,301 A * | 3/1979 | Strauss et al. .................. 315/73 |
| 4,158,792 A * | 6/1979 | Kuroi et al. .................... 315/86 |
| 4,348,612 A | 9/1982 | Morton |
| 4,458,136 A | 7/1984 | Wagatsuma |
| 4,538,094 A * | 8/1985 | Perper ......................... 315/221 |
| 4,609,852 A * | 9/1986 | Perper ......................... 315/278 |
| 4,683,523 A * | 7/1987 | Olsson et al. ............... 362/477 |
| 4,808,877 A | 2/1989 | Netten et al. |
| 4,812,702 A | 3/1989 | Anderson |
| 4,894,591 A | 1/1990 | Witting |
| 4,977,354 A | 12/1990 | Bergervoet et al. |
| 5,030,125 A * | 7/1991 | Toma et al. .................. 439/226 |
| 5,039,903 A | 8/1991 | Farall |
| 5,105,119 A | 4/1992 | Dayton |
| 5,122,729 A | 6/1992 | Itoga et al. |
| 5,184,891 A | 2/1993 | Shpigel |
| 5,229,652 A | 7/1993 | Hough |
| 5,264,997 A | 11/1993 | Hutchisson et al. |
| 5,289,085 A | 2/1994 | Godyak et al. |
| 5,300,860 A | 4/1994 | Godyak et al. |
| 5,301,096 A | 4/1994 | Klontz et al. |
| 5,345,149 A | 9/1994 | Ham |
| 5,422,519 A | 6/1995 | Russell |
| 5,434,763 A * | 7/1995 | Hege et al. .................. 362/265 |
| 5,450,305 A | 9/1995 | Boys et al. |
| 5,536,979 A | 7/1996 | McEachern et al. |
| 5,550,452 A | 8/1996 | Shirai et al. |
| 5,594,304 A | 1/1997 | Graber |
| 5,675,677 A | 10/1997 | Davenport et al. |
| 5,828,174 A * | 10/1998 | Seiler et al. .................... 315/62 |
| 5,834,905 A | 11/1998 | Godyak et al. |
| 5,905,343 A * | 5/1999 | McCamant .................. 315/57 |
| 5,923,544 A | 7/1999 | Urano |
| 5,928,505 A | 7/1999 | Inakagata et al. |
| 5,929,598 A | 7/1999 | Nakama et al. |
| 5,949,155 A | 9/1999 | Tamura et al. |
| 5,952,814 A | 9/1999 | Van Lerberghe |
| 6,005,304 A | 12/1999 | Seelig |
| 6,028,413 A | 2/2000 | Brockmann |
| 6,118,249 A | 9/2000 | Brockmann et al. |
| 6,188,179 B1 | 2/2001 | Boys et al. |
| 6,194,828 B1 | 2/2001 | Kohne et al. |
| 6,241,359 B1 | 6/2001 | Lin |
| 6,275,143 B1 | 8/2001 | Stobbe |
| 6,339,296 B1 | 1/2002 | Goral |
| 6,456,015 B1 * | 9/2002 | Lovell et al. ................ 315/248 |

FOREIGN PATENT DOCUMENTS

| | | |
|---|---|---|
| DE | 4100272 | 7/1991 |
| DE | 9012505 | 8/1991 |
| EP | 0357829 | 3/1990 |
| EP | 1063468 | 12/2000 |
| GB | 1349788 | 4/1974 |

* cited by examiner

INDUCTIVELY POWERED SECONDARY ASSEMBLY

RELATED APPLICATIONS

The present invention is a continuation of U.S. application Ser. No. 10/,977,443, now U.S. Pat. No. 7,153,178, filed Oct. 29, 2004, which is a continuation of U.S. application Ser. No. 10/455,694, now U.S. Pat. No. 6,831,417, filed Jun. 5, 2003, which is a division of U.S. application Ser. No. 10/133,860, now U.S. Pat. No. 6,731,071, filed Apr. 26, 2002, which claims the benefit of U.S. Provisional Application No. 60/357,908, entitled Point of Use Water Treatment System, filed Feb. 19, 2002 and is a continuation-in-part of U.S. application Ser. No. 09/592,194 entitled Fluid Treatment System, which was filed on Jun. 12, 2000, now U.S. Pat. No. 6,436,299, which claims benefit of U.S. Provisional Application Ser. No. 60/140,159, entitled Water Treatment System Within Inductively Coupled Ballast, filed Jun. 21, 1999, and which claims the benefit of U.S. Provisional Application Ser. No. 60/140,090, entitled Point-Of-Use Water Treatment System, filed Jun. 21, 1999.

BACKGROUND OF THE INVENTION

The present invention relates to lighting and more particularly to a lamp assembly for use in connection with inductively powered lighting.

Although not widely available, inductively coupled lighting systems are known. A conventional inductively coupled lighting system generally includes a primary circuit having a primary coil (or "primary") that is driven by a power supply and a secondary circuit having a secondary coil (or "secondary") that inductively receives power from the primary. Inductive couplings provide a number of advantages over conventional direct electrical connections. First, inductively coupled lamps are typically safer and easier to connect and disconnect than hardwired lamps. With direct electrical connections, it is generally necessary to manipulate electrical connectors when installing and removing the lamp assembly. This typically requires some effort and creates a risk of electrical shock. Often, the electrical connectors are at least partially exposed, thereby increasing the risk of electrical shock. Inductively coupled lamps, on the other hand, do not require the manipulation of any electrical connectors. Instead, the secondary of the lamp assembly simply needs to be placed adjacent to the primary to permit the supply of power to the lamp assembly. Second, the elimination of electrical connectors also increases the reliability of the system by eliminating the problems associated with conventional electrical connectors. For example, conventional electrical connectors are subject to corrosion and to wear. These problems are particularly acute in an outdoor setting where environmental conditions may subject the electrical connectors to moisture. With repeated use, mechanical connectors are also subject to wear and eventual failure. Third, inductively coupled lamps inherently provide a lower risk of an electrical hazard at the lamp assembly. As noted above, the lamp assembly is electrically separated from the power source. All power must be inductively passed from the power source to the lamp assembly. Because there is an intrinsic limit on the amount of power that can be inductively passed to the lamp assembly, the amount of power at the lamp assembly is limited and the risk of electrical hazard is reduced.

Although conventional inductively coupled lamps provide a number of important advantages over directly connected lamps, they do suffer significant drawbacks. An inductive coupling is inherently less efficient than a direct electrical connector. This is partly due to the power required to create and sustain the electromagnetic field. The primary inefficiencies in a conventional inductive coupling result from a poorly tuned circuit. These inefficiencies are manifest in increased heat gain and in noise created by vibration in the primary and secondary. The efficiency issues are exaggerated with higher power lighting applications. In addition, existing lamp circuits require precise alignment of the primary and secondary to provide any reasonable level of efficiency. This requires more precise tolerances and limits the configuration and layout of the lamp assembly and the overall lamp.

One of the largest reliability issues facing the lamp industry is caused by the penetration of the lamp sleeve by wires or other electrical conductors. Typically, the wires pass into the interior of the lamp through a glass stem. Because glass does not readily adhere to and seal around the wires, there is a material risk of lamp leakage at the point the wires penetrate the lamp. Although efforts have been made to optimize the seal, this remains a significant reliability concern.

With conventional inductively powered lamps, there are also reliability issues associated with exposure of the lamp circuit components to the environment, for example, water and moisture from the environment can damage circuit components. To address this concern, at least one inductively powered lighting system encloses the entire lamp assembly without a sealed enclosure. U.S. Pat. No. 5,264,997 to Hutchisson et al discloses a lamp that is mounted to a printed wiring board that is spaced from the secondary on a plurality of posts. The printed wiring board includes various electrical component required for operation of the inductive coupling. Separate shell and lens components are sealed together to form a leaktight enclosure around the lamp, the printed wiring board and the secondary. The shell is specially shaped to receive the secondary and to be interfitted with a socket containing the primary. Although the sealed enclosure provides improved protection from environmental conditions, it is relatively bulky and only provides light transmission in the direction of the lens.

As can be seen, there remains a need for an inductively coupled lamp assembly that is efficient, provides improved reliability in a variety of conditions and is easily adapted to many different lamp configurations.

SUMMARY OF THE INVENTION

The aforementioned problems are overcome by the present invention wherein a capacitor. The capacitor is connected in series with the lamp and the secondary, and is selected to have a resistance at the operating frequency that is approximately equal to or slightly less than the combined impedance of the lamp and the secondary at operating temperature. As a result, the lamp circuit operates at or near resonance. With electric-discharge lamps, the series capacitor also functions to limit the flow of current in the secondary circuit, precluding an uncontrolled increase in current that would otherwise occur with an electric discharge lamp.

In another aspect, the present invention provides an inductively powered lamp assembly in which the entire lamp assembly circuit is sealed within a transparent sleeve. Preferably, the entire lamp assembly circuit, including secondary and any associated capacitor is sealed within the sleeve of the lamp. In an alternative embodiment, the secondary and lamp, as well as any capacitor and starter device, are contained within a second closed plastic, Teflon, glass or quartz sleeve with no wires or other elements penetrating the sleeve. The void defined between the second sleeve and the lamp sleeve is preferably evacuated or filled with a functional gas to provide the desired level of heat conduction or insulation.

In a further aspect, the present invention provides a remotely actuated switch to provide preheat of electric-discharge lamp. The switch is provided to short the electrodes across the secondary for a specific period of time at lamp start-up. In addition this circuit may have a series resistor to help limit preheat current. In one embodiment, the switch is an electromagnetic switch that is preferably actuated by a magnetic field generated by a corresponding coil in a lamp control circuit.

The present invention provides a simple and inexpensive lamp assembly for use with inductively powered lighting. Because the lamp assembly operates at or near resonance, it has a high power factor and is highly efficient. This reduces power loss through heat build up and also provides for quiet operation of the inductive coupling—even in relatively high power applications. The efficiency of the secondary circuit demands less precise alignment between the primary and secondary, thereby permitting a greater degree of latitude in the layout and configuration of the lamp and the lamp assembly. The sealed sleeve provides the lamp circuit with improved protection from the environment without limiting the transmission of light from the lamp. Although with some light sources, the spectrums emitted may see losses based on the specific transmissive properties of the materials used in the sleeves, for example, some materials are not highly transmissive to UV light. The present invention allows functional gases to be entrapped within the sealed sleeve to increase or reduce the degree to which the lamp is isolated from the environment. Further, by enclosing the entire lamp circuit within the lamp sleeve, the need for wires or electrical leads that penetrate the sleeve can be eliminated. This greatly improves the reliability of the lamp while dramatically reducing manufacturing losses. Also, the electromagnetic switch of the present invention provides an inexpensive and reliable alternative to conventional starter circuits.

These and other objects, advantages, and features of the invention will be readily understood and appreciated by reference to the detailed description of the invention and the drawings.

DETAILED DESCRIPTION OF INVENTION

Figure 1:
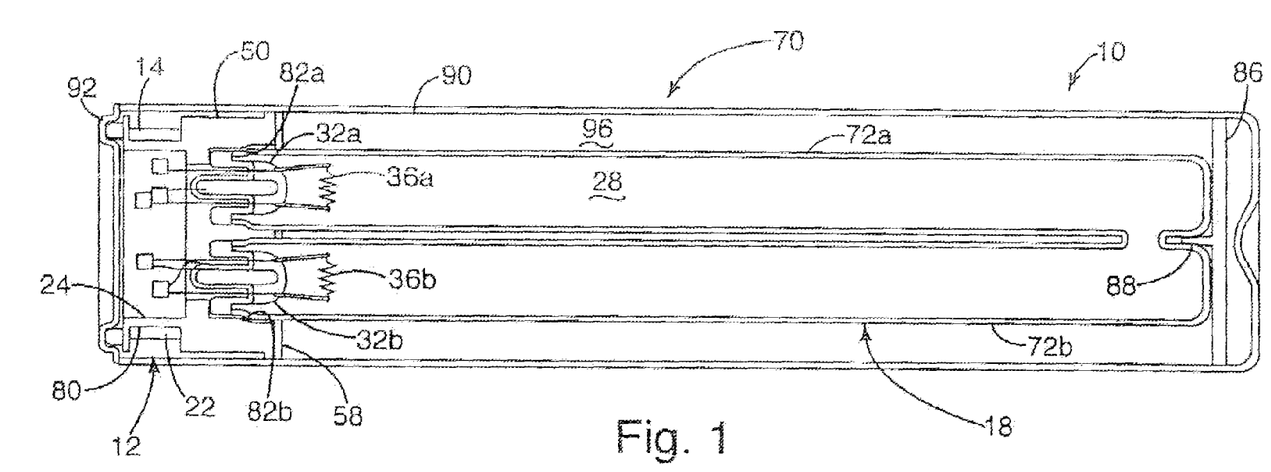
FIG. 1 is a sectional view of a lamp assembly according to one embodiment of the present invention.
Figure 2:
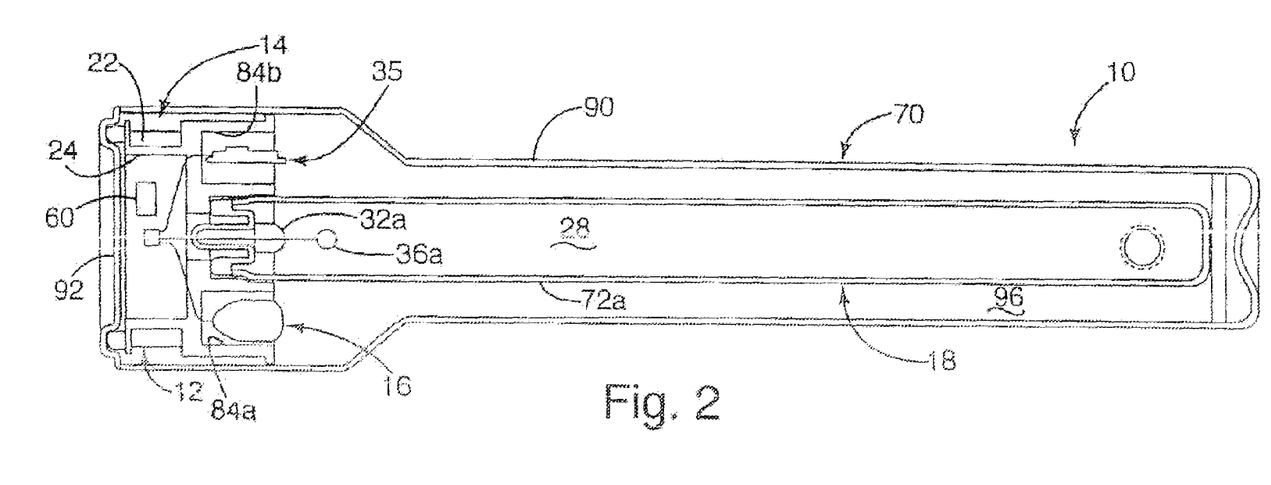
FIG. 2 is a sectional view the lamp assembly of FIG. 1 taken perpendicularly to the sectional view of FIG. 1.

A lamp assembly according to an embodiment of the present invention is shown in FIGS. 1 and 2, and is generally designated 10. For purposes of disclosure, the present invention is first described in connection with a conventional type PL-S 11 watt UV lamp converted for use at 38 watt, such as the type used in a water treatment device. The lamp assembly 10 generally includes a lamp circuit 12 and an outer sleeve 70. The lamp circuit 12 includes a secondary 14, a capacitor 16 and a lamp 18, all connected in series (see FIG. 3). The secondary 14 inductively receives power fro the primary (not shown) of an associated ballast (not shown). The series capacitor 16 is specially tuned, as described in more detail below, so that the lamp circuit operates at resonance under specific operating conditions. The entire lamp circuit 12 is fully enclosed within the outer sleeve 70, including the secondary 14, capacitor 16 and lamp 18. At least a portion of the outer sleeve 70 is transparent and is not penetrated by electrical wires or other elements.

Although the following embodiment is described in connection with a type PL-S 38 watt UV lamp, the present invention is intended and well suited for use with lamps of various types and styles, including electric-discharge, incandescent, pulsed white light and light emitting diode ("LED") lamps. This disclosure presents various alternative embodiments showing incandescent lamps and electric-discharge lamps. These examples are provided to illustrate the broad applicability and adaptability of the present invention, and not to provide any limit on the scope of the claims.

A wide variety of ballasts capable of powering the inductive lamp assembly of the present invention are well known to those skilled in the field. Accordingly, the ballast will not be described in detail. One ballast particularly well-suited for use with the type PL-S 38W UV lamp of the illustrated embodiment is disclosed in U.S. application Ser. No. 90/592,194 entitled "Fluid Treatment System," which was filed on Jun. 12, 2000, which is incorporated herein by reference in its entirety. This ballast can be readily adapted to provide efficient operation of all of the disclosed embodiments of the present invention.

I. Lamp Configuration

As noted above, the type PL-S 38W UV lamp preferably includes an outer sleeve 70 that encloses the lamp circuit 12 to protect it from the environment (See FIGS. 1 and 2). The outer sleeve 70 preferably includes a main body 90 and a cap 92.

The main body 90 is a generally cylindrical tube having an open end and a closed end. After the lamp circuit 12 is installed within the main body 90, the cap 92 is sealed over the open end of the main body 90 to fully enclose the lamp circuit 12. The lamp circuit 12 generally includes a secondary 14, a capacitor 16 and a lamp 18. As described below, the lamp circuit 12 may also include a starter 35 (See FIG. 2). The lamp 18 is a generally conventional PL-S type lamp having a quartz sleeve with two parallel legs 72a-b that are interconnected to cooperatively define a chamber 28. The chamber 28 is partially evacuated and contains the desired electric-discharge gas, such as mercury vapor. A stem 32a-b is located at the base of each leg 72a-b. A pair of conventional or custom designed electrodes 26a-b are disposed within the chamber 28, one mounted atop each of the stems 32a-b. In this embodiment, the outer sleeve 70 is preferably manufactured from quartz to permit the efficient passage of UV light. In non-UV applications, the outer sleeve may be manufactured from glass, Teflon or plastic, depending in part on the heat generated by the lamp and the operating environment of the lamp. For example, an alternative outer sleeve can be manufactured from a length of Teflon tubing having sealed opposite ends (not shown). The Teflon tubing can be fitted over the remainder of the lamp assembly, and its opposite ends can be crimped or otherwise sealed to close the Teflon sleeve. Preferably, each end of the Teflon tubing is folded back onto itself and crimped using heat and pressure.

The lamp assembly 10 also includes a base 50 and a support 86 that hold opposite ends the lamp 18 within the outer sleeve 70. The base 50 is generally cylindrical and dimensioned to be fitted closely within the outer sleeve 70. In addition to holding one end of the lamp 18, the base 50 also receives the various electrical components of the lamp circuit 12. The base 50 defines an annular recess 80 to receive the windings of the secondary 14, a pair of apertures 82a-b to receive the base end of each leg 72a-b, and a pair of voids 84a-b to contain the capacitor 16 and any desired starter 35. The lamp assembly 10 may also include a heat reflector 58 disposed between the secondary and the electrodes 36a-b. The heat reflector 58 is preferably shaped to match the cross-sectional shape of the lamp sleeve 52 at the point where it is mounted, and is preferably manufactured from a conventional reflective material, such as aluminum or aluminum foil on a suitable substrate. The support 86 is generally disc-shaped and is dimensioned to be fitted closely within the outer sleeve 70. The support 86 preferably includes a tab 88 to be fictionally fitted between the legs 72a-b of the quartz sleeve 52. The precise design and configuration of the base 50 and support 86 can vary among applications depending on the design and configuration of the outer sleeve 70 and the various components of the lamp circuit 12. The base 50 and support 86 are preferably manufactured from materials capable of withstanding high heat, such as ceramic or high temperature plastics.

In one embodiment, the void 96 defined between the outer sleeve 70 and the lamp sleeve 52 is configured to provide the lamp assembly with the desired conductive or insulative properties. For example, this void 96 can be evacuated to insulate the lamp from cold environments. Alternatively, the void 96 can be filled with heavier gases, such as argon and neon, or fluids to conduct heat in hot environments. The conduction of heat from lamps in hot environments will help to protect the lamp from overheating and may also help to provide maximum intensity.

In some applications, the lamp assembly 10 may also include a mechanism that permits the ballast to sense the presence of the lamp assembly 10. This permits the ballast to power the primary (not shown) only when the lamp assembly 10 is installed. Although the sensing mechanism is not necessary in many applications, particularly in low-power applications, it does provide a more efficient design that conserves power, reduces heat build-up and protects the primary from certain types of damage associated with continuous operation. In one embodiment, the lamp assembly 10 includes a sensing magnet 60 and the ballast (not shown), or an associated control circuit, includes a reed switch (not shown) that is activated by the sensing magnet 60. More preferably, when the lamp assembly 10 is installed, the sensing magnet 60 is positioned adjacent to reed switch (not shown). The magnetic field from the sensing magnet 60 causes the reed switch 62 to close, thereby providing a signal to the ballast or control circuit that the lamp assembly 10 is in place. The sensing magnet is preferably mounted to the base 50, but may be mounted in other locations as desired. Alternatively, the sensing magnet 60 and reed switch (not shown) can be replaced by a mechanical switch (not shown). For example, a switch can be disposed where it is mechanically closed by installation of the lamp assembly 10. Another alternative is to provide the lamp with a manually actuated on/off switch, for example, a toggle switch, that selectively turns the ballast on and off.

II. Lamp Circuit

Figure 3:
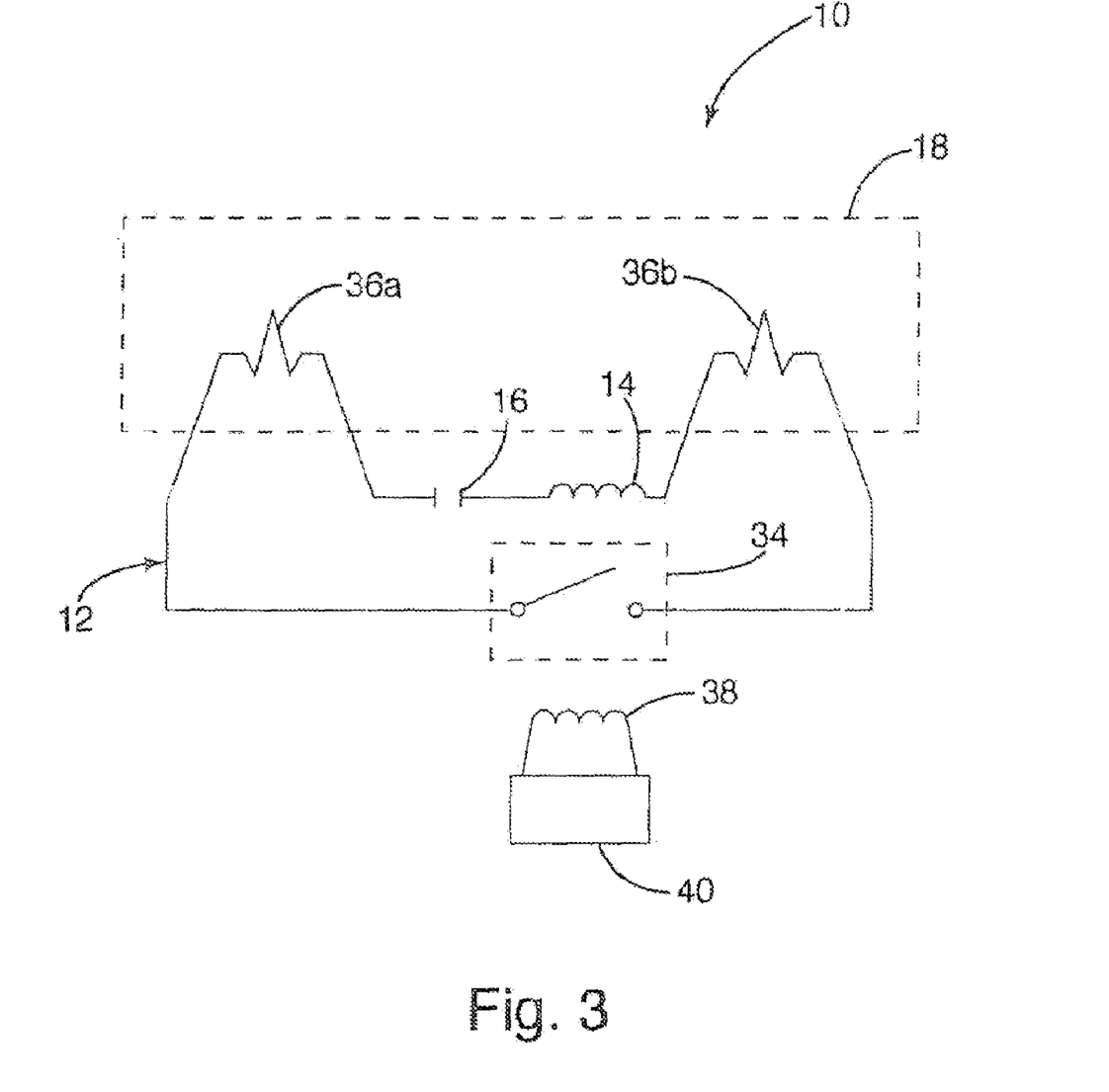
FIG. 3 is a schematic diagram of a lamp circuit according to one embodiment of the present invention.

The lamp circuit 12 will now be described in connection with the type PL-S 38W UV lamp described above (See FIGS. 1 and 2). As noted above, the lamp circuit 12 generally includes a lamp 18, a secondary 14 and a capacitor 16. A schematic diagram of a lamp circuit 12 is shown in FIG. 3. In this embodiment, the lamp circuit 12 includes a single secondary 14, preferably in the form of a coil of small diameter wire 22. The precise characteristics of the secondary 14 will vary from application to application as a function of the primary (not shown) and the load (e.g. the lamp). The wire 22 is preferably conventional magnet or LITZ wire depending on the power settings and heat dissipation. The wire is preferably wrapped around the base 50 within the annular recess 80, which provides the secondary 14 with a hollow core. If desired, the hollow core 24 can be replaced by other conventional cores. The type of wire, the number of turns of wire and the diameter of the core (and consequently the diameter of the turns of wire) will vary from application to application, depending on various factors such as the characteristics of the primary and the load of the lamp 18. The inductance of the secondary 14 is selected as a function of the operating frequency and the impedance of the load (i.e. the lamp) at the supplied power. More specifically, the inductance of the secondary 14 is determined by the following formula:

$$\text{Inductance of the Secondary} = \frac{\text{Impedance of the Load}}{2\pi \times \text{Operating Frequency}}$$

In the described 38 watt embodiment, the secondary 14 is configured to receive power from a primary operating at approximately 100 kilohertz. The secondary 14 includes 72 turns of wire and the primary includes 135 turns of wire. In the described 38 watt embodiment, the secondary 14 has a value of 196 microhenries at 100 kilohertz, having a reactance of approximately 123 ohms. The secondary 14 is preferably located within the base 50 of the lamp assembly 10. The diameter of the secondary 14 is preferably selected to closely fit with the base 50. The secondary 14 is electrically connected to lamp 18 by leads 51a-b. Although the secondary 14 is preferably circular, it may vary in shape form from application to application. For example, the secondary may be square, oval, triangular, trapezoidal, hexagonal or even spherical. The secondary is preferably positioned internally or externally concentric to the primary, or the two coils may be placed end to end.

The capacitor 16 is selected to provide optimum power factor correction given to the mechanical constraints, thereby providing resonance in the lamp circuit 12. The power factor is preferably 0.90 or better, and more preferably 0.96 or better, but in some applications lower values may be acceptable. Without sufficient power factor correction, the reactive currents in the secondary will reflect back into the primary as a lower impedance load. This would cause a shift upward in operating power and current, as well as higher losses in the form of heat gain in the primary circuit. This effect is contrary to what one might initially expect but is in fact due to the inverse nature of reflected impedance within a series resonant primary circuit. Experience has revealed that reactive currents and losses in the primary increase very quickly at factors below 0.90. This can have a material adverse impact on efficiency, especially when it is considered that these losses are additive to the losses caused by coupling coefficient and dc resistances. In general, the capacitor 16 is selected to have a reactance that is approximately equal to or slightly less than the resistive impedance of the lamp 18 and the reactive impedance of the secondary 14 when the lamp 18 is at its operating temperature. Like the inductance of the secondary 14, the reactance of the capacitor is selected as a function of the operating frequency and the impedance of the load (i.e. the lamp at the supplied power. More specifically, the reactance of the capacitor is selected in accordance with the following formula:

$$\text{Reactance of the Capacitor} = \frac{1}{\text{Impedance of the Load} \times 2\pi \times \text{Operating Frequency}}$$

At this reactance, the capacitor 16, secondary 14 and lamp 18 will be operating close to resonance, providing a high power factor and consequently high efficiency. In the illustrated embodiment, the capacitor 16 has a value of approximately 12.9 nanofarads (nf). This value will change in response to variations in the primary (not shown), secondary 14 and/or lamp 18.

The secondary and capacitor formulas presented above provide a rough approximation of the desired capacitor and secondary reactance values. To provide more refined values (and thereby fine-tune the power factor, current limiting effect, and overall operating parameters), an iterative testing procedure may be employed. This iterative testing may be required in some applications to provide the desire level of efficiency in the secondary circuit. The operating parameters of these designs include preheat, strike voltage, and operating current. All of these parameters can be configured through this tuning process along with changes in values of ratios, capacitance and inductance.

Although the capacitor 16 is preferably tuned to the secondary 14 and lamp 18 when the lamp 18 is at operating temperature, the capacitor 16 can alternatively be tuned to provide optimum efficiency at other times. For example, in electric-discharge lamps where greater current is required to start the lamp, the present invention can be employed to boost the circuit during start-up. In such applications, the capacitor is selected to have a reactance that is approximately equal to the combined impedance of the secondary and the lamp at start-up temperature (rather than at operating temperature). This will increase the efficiency of the lamp circuit during start-up, permitting the use of a ballast with a lower current maximum.

Given the nature of plasma, electric-discharge lamps attempt to maintain voltage at a substantially constant inherent voltage. As a result, if the secondary 14 generates voltage in excess of the inherent voltage of the lamp, the lamp will attempt to consume the excess power. Because the resistance of in an electric-discharge lamp decreases in response to the flow of current, the lamp has the potential to drawing increasingly more current until the circuit limits or self-destructs. This concern is addressed by the capacitor 16, which functions to limit the current supplied to the lamp. The current limiting function is an inherent characteristic of a capacitor. It has been determined that the capacitor value required to place the secondary circuit at resonance is approximately equal to the capacitor value needed to provide appropriate current limiting. Accordingly, it has been determined that the current limiting function is achieved in the present invention by selecting a capacitor value appropriate to provide unity power factor.

When the present invention is incorporated into an electric-discharge lamp assembly, the lamp circuit 12 preferably includes a conventional starter 35 (See FIG. 2), glow bulb or other equivalent mechanism. Starters and glow bulbs are well known and will therefore not be described in detail in this application. In one embodiment of an electric-discharge lamp assembly, the conventional starter is replaced by a remotely actuatable switch, such as electromagnetic switch 34 (See FIG. 3). The electromagnetic switch 34 is wired in series between the electrodes 36a-b, thereby selectively permitting the switch 34 to close the circuit between the electrodes 36a-b. When closed, the switch 34 permits current to flow directly through the electrodes 36a-b, rather than through requiring it to arc through the gas. As a result, when the switch 34 is closed, the electrodes 36a-b are rapidly heated. The electromagnetic switch 34 is preferably arranged substantially perpendicular to the field of the primary so that the electromagnetic switch 34 is not actuated by the electromagnetic field of the primary. Instead, a separate coil 38 is positioned adjacent to the electromagnetic switch 34 where it can be charged to selectively close the switch 34. A microprocessor 40 preferably controls operation of the coil 38 and therefore the electromagnetic switch 34. The microprocessor 40 is programmed to charge the coil 38 for a fixed period of time each time that the lamp circuit is powered on. This closes the electromagnetic switch 34 shorting the electrodes 36a-b together. Alternatively, the microprocessor 40 can be replaced by a conventional one-shot timer circuit (not shown) that is configured to charge the coil for the desired period of time each time that the lamp is started.

III. Alternative Embodiments

The configuration of the lamp assembly may vary materially from application to application depending largely on the type of lamp and the associated power requirements. The present invention can be readily modified to permit use with a wide variety of existing lighting systems. The following alternative embodiments describe a variety of alternative embodiments adapted for various uses. These alternative embodiments are intended to be illustrative of the wide adaptability of the present invention, and not intended to be exhaustive.

Figure 4:
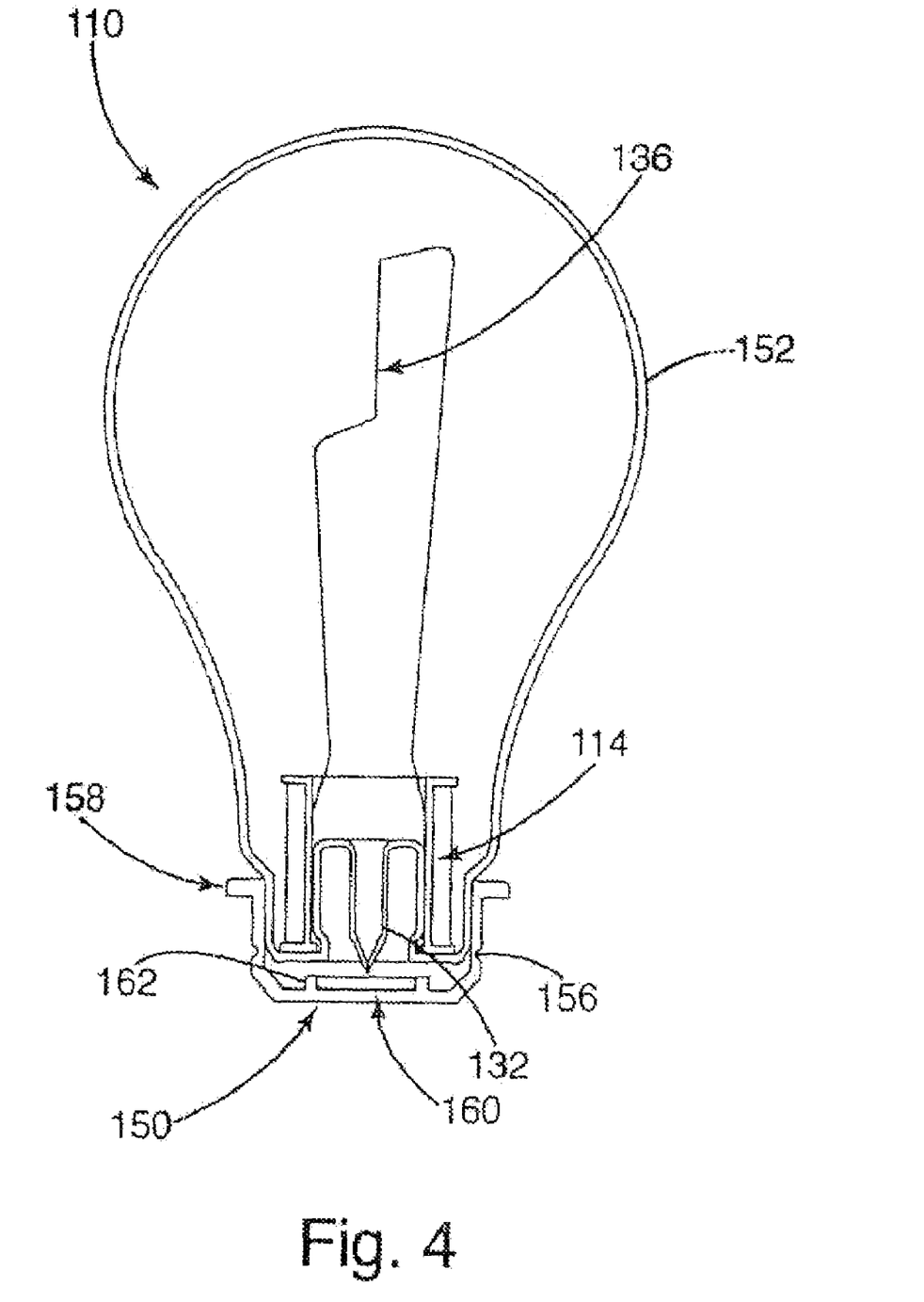
FIG. 4 is a sectional view of an alternative lamp assembly having an incandescent lamp with a universal base.
Figure 5:
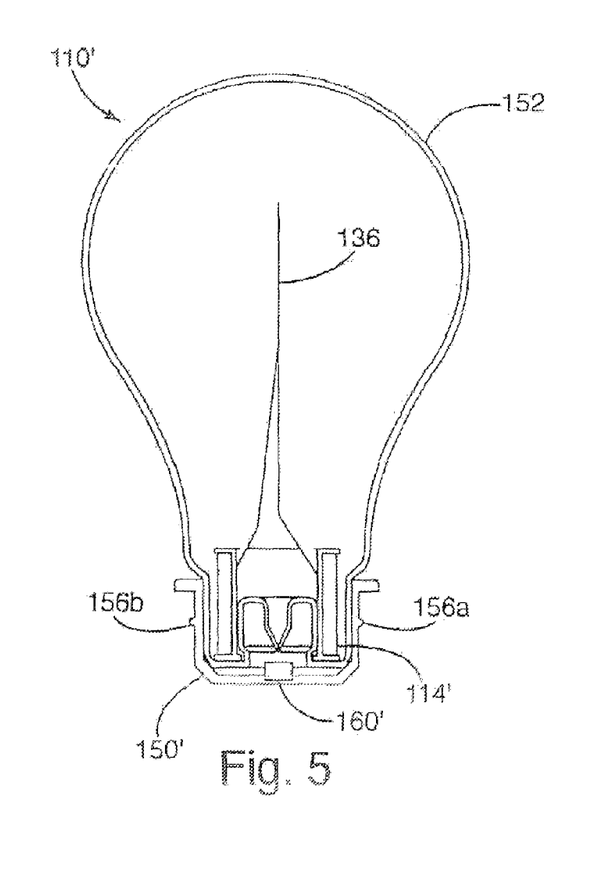
FIG. 5 is a sectional view of an alternative lamp assembly having an incandescent lamp with a universal base.

An alternative embodiment showing the present invention incorporated into an incandescent lamp is shown in FIG. 4. In this embodiment, the lamp assembly 110 includes a glass sleeve 152 and a plastic base 150. The glass sleeve 152 is generally bulb shaped and includes an inwardly turned and generally cylindrical stem 132. A secondary 114 is mounted within the glass sleeve 152 about stem 132. A filament 136 is mounted to the secondary 114 extending upwardly into the bulbous portion of the glass sleeve 152 in a conventional manner. Unlike the embodiment described above, the base 150 in this embodiment is fitted to the outside of the glass sleeve 152. The base 150 is configured to be interfitted with a corresponding socket (not shown). The illustrated base 150 is generally circular and includes an annular recess 156 configured to snap fit into a corresponding socket (not shown). The base 150 also includes an upper flange 158 that provides a gripping edge for removing the lamp assembly 110 from a socket (not shown). The base 150 may, however, take on a variety of different configurations to permit the lamp assembly 110 to mechanical connect to a variety of different sockets. For example, the base may be externally threaded. As illustrated, lamp assembly 110 also preferably includes a sensing magnet 160. The sensing magnet 160 may be fitted into a corresponding retaining wall 162 in the bottom of base 150. As described above, the sensing magnet 160 functions with a magnetically actuated switch, such as a reed switch, to advise the primary or control circuit of the presence of the lamp assembly 110. This permits the primary to be powered only when a lamp assembly 110 is in place. As shown in FIG. 5, the incandescent lamp assembly 110' can be configured to operate with a conventional universal base. In this embodiment, the base 150' includes a pair of mounting pins 156a-b that are configured to interlock with matching slots in a conventional universal base lamp socket (not shown).

Figure 6:
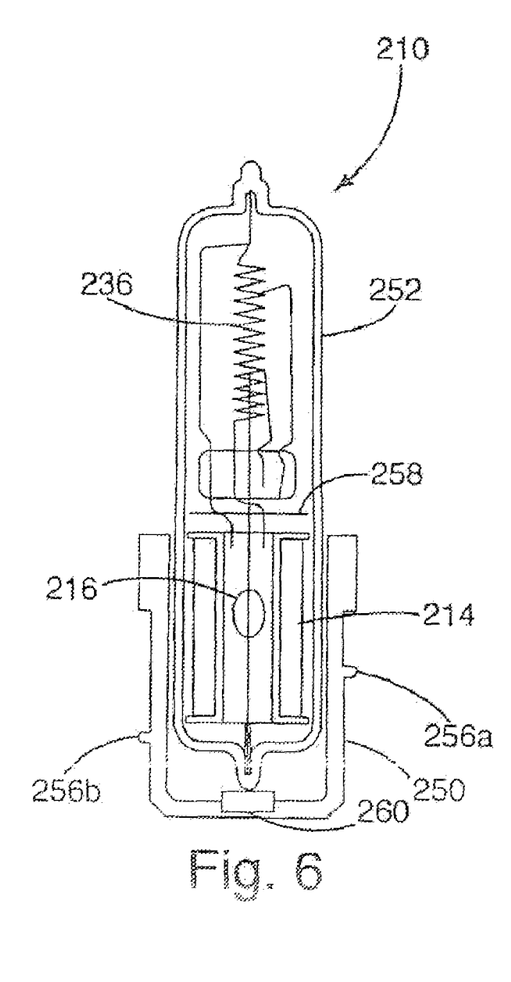
FIG. 6 is a sectional view of an alternative lamp assembly having a halogen lamp.

An alternative embodiment showing the present invention incorporated into a halogen lamp is shown in FIG. 6. In this embodiment, the lamp assembly 210 generally includes a quartz sleeve 252 and a ceramic base 250. The materials of the sleeve 252 and base 250 are selected to withstand the particularly high temperature at which halogen lamps operate. The quartz sleeve 252 is preferably fully sealed and does not include any penetrating elements, such as wires or other electrical connectors. A filament 236, secondary 214 and capacitor 216 are enclosed within the quartz sleeve 252. In some applications, the capacitor 216 may not be necessary to provide an acceptable level of efficiency and may accordingly be eliminated. The lamp assembly 210 further includes a heat reflector 258 disposed between the filament 236 and the secondary 214. The base 250 may include quarter turn threads 256a-b that are threadedly interfitted within a corresponding socket (not shown). The base 250 can be provided with alternative structure to facilitate installation in the socket. A sensing magnet 260 is preferably mounted to the inside bottom surface of the base 250.

Figures 7, 9:
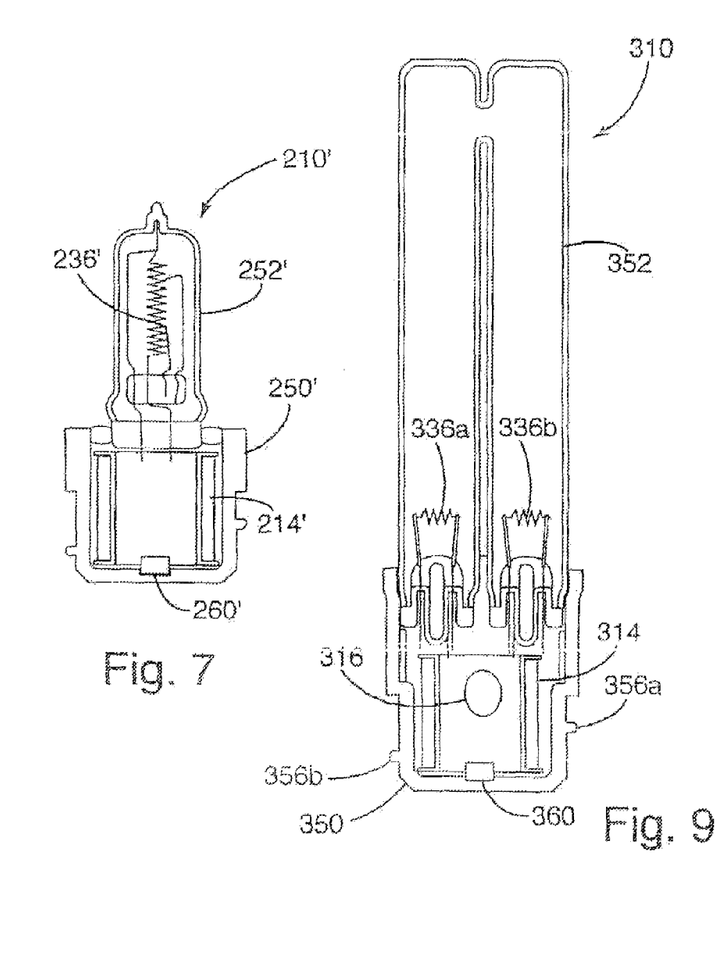
FIG. 7 is a sectional view of an alternative lamp assembly having a halogen lamp with the base located outside of the lamp sleeve.
FIG. 9 is a sectional view of an alternative lamp assembly having a fluorescent lamp with no outer sleeve.

In an alternative halogen lamp assembly 210', the quartz sleeve 252' is shortened to terminate just within the neck of the base 250' (See FIG. 7). The secondary 214' is moved outside of the quartz sleeve 252' and is positioned in the base 250'. In this embodiment, the secondary 214' is isolated from the heat of the filament 236'. This embodiment may also include a sensing magnet 260'.

Figure 8:
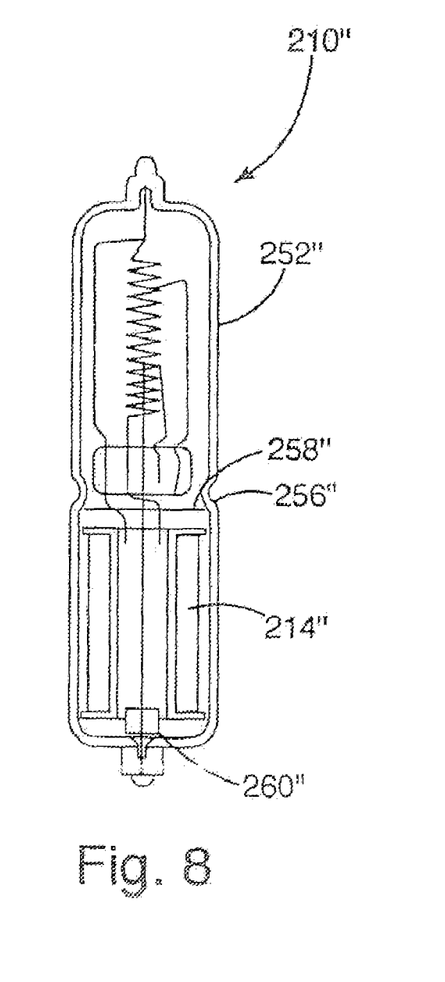
FIG. 8 is a sectional view of an alternative lamp assembly having a halogen lamp with no base.

In another alternative halogen lamp assembly 210", the base is eliminated and the sensing magnet 260"is moved into the interior of the sealed quartz sleeve 252". As shown in FIG. 8, the quartz sleeve 252" defines an annular recess 256" that extends entirely around the sleeve 252" to permit the lamp assembly 210" to be snap-fitted into a corresponding socket (not shown).

Another alternative embodiment is shown in FIG. 9. In this embodiment, the lamp assembly 310 includes a base 350 that is disposed outside of the lamp sleeve 352 and the lamp assembly 310 does not include an outer sleeve. The lamp sleeve 352 encloses the electrodes 336a-b and the desired electric-discharge gas, for example, mercury vapor. The secondary 314, capacitor 316, any desired starter mechanism (such as a conventional starter or the magnetically actuated switch described above) and all electrical connections are contained inside the base 350, but outside of the lamp sleeve 352. The base 350 is configured to corresponding with a conventional universal base, and includes a pair of mounting pins 356a-b that interlock with matching slots in the lamp socket (not shown). The base 350 may alternatively be configured to match with other socket configurations. A sensing magnet 360 is preferably mounted in the base 350. If desired, an outer sleeve (not shown) can be added to this lamp assembly 310 to enhance its protection from the environment. If included, the outer sleeve would preferably extend around the entire lamp assembly, except for the base 350. The base 350 would mounted to the exterior of the outer sleeve where it can be interfitted with a lamp socket.

Figure 10:
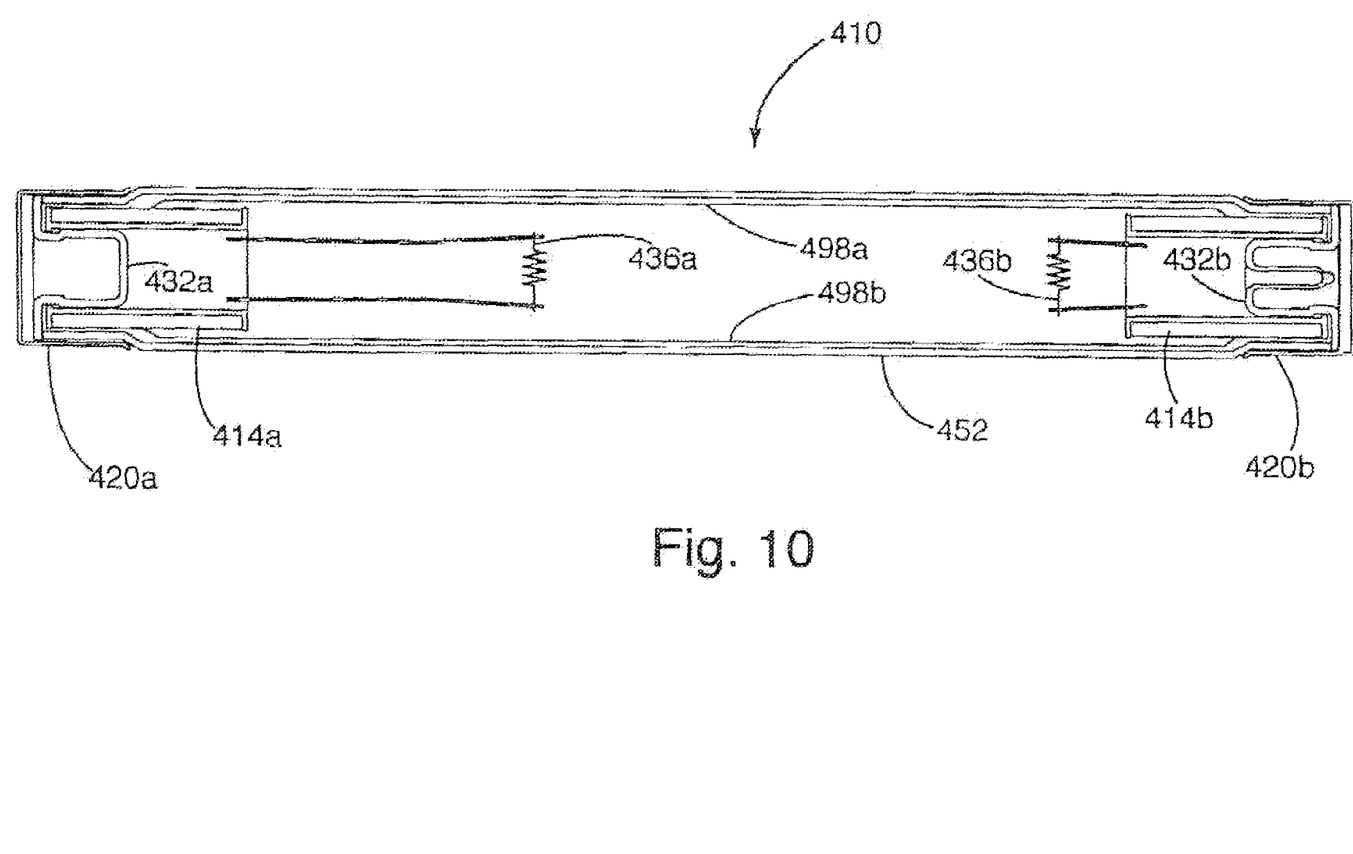
FIG. 10 is a sectional view of an alternative lamp assembly having a type T-5 or T-8 fluorescent lamp.
Figure 11:
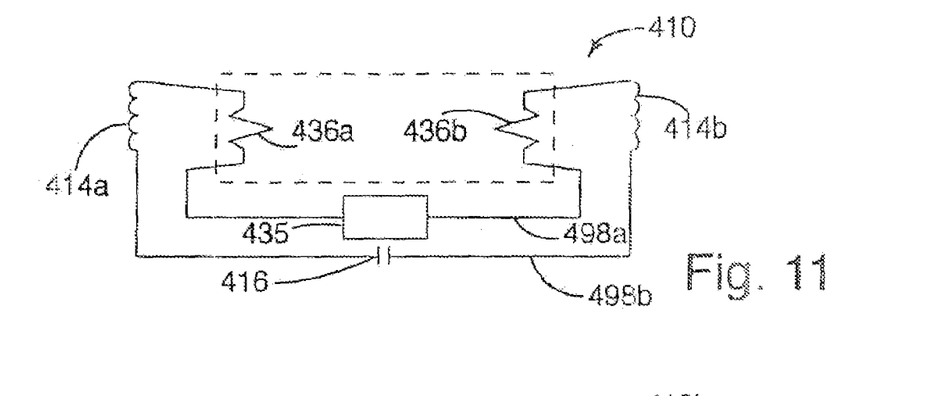
FIG. 11 is a schematic diagram of a lamp circuit for the lamp assembly of FIG. 10.
Figure 12:
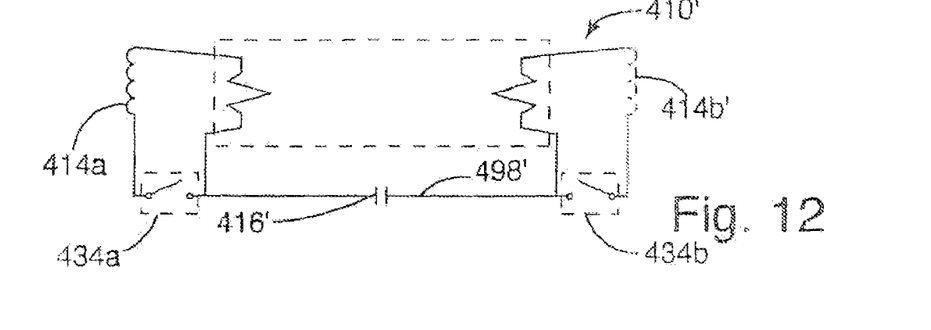
FIG. 12 is a schematic diagram of an alternative lamp circuit for the lamp assembly of FIG. 10.

An alternative embodiment showing the present invention incorporated into a type T5 or T8 fluorescent lamp is shown in FIGS. 10 and 11. The lamp assembly 410 includes an elongated glass sleeve 452 and a pair of secondaries 414a-b-one located at each end of the sleeve 452. Given the different physical location of the two secondaries 414a-b, the power supply is preferably configured to include two separate primaries (not shown) that separately power the two secondaries 414a-b. The two primaries are disposed adjacent to the corresponding secondary 414a-b. It is typical to evenly distribute the power between the coils 414a-b, but is not strictly necessary. Preferably, the secondary coils 414a-b are set to opposite polarity with each primary and secondary combination being configured to sustain half of the voltage and current needed to power the lamp. The sleeve 452 preferably includes an annular stem 432a-b formed at each opposite end to receive the secondaries 414a-b. An electrode 436a-b is electrically connected to each secondary 414a-b. A capacitor 416 is connected in series between the two secondaries 414a-b. The preferred method for calculating the value of the capacitors 416a-b in this embodiment is to initially analyze the circuit as though only a single coil was going to be used in accordance with the methodology described above (in connection with the first disclosed embodiment). The value of the single capacitor of this hypothetical configuration is then halved to provide the value for each of the two capacitors 416a-b of this embodiment. Optional end caps 420a-b, preferably of aluminum, are fitted over opposite ends of the sleeve 452. The lamp assembly 410 may include a conventional started 435 as shown in FIG. 11. In this embodiment, conductors 498a-b are required to extend between the two secondary coils 414a-b. The conductors 498a-b are preferably contained within the lamp sleeve 452. As an alternative, magnetic switches 434a-b, or other remotely actuated switches, are used in place of a conventional starter. As shown in FIG. 12, the lamp assembly 410' includes a separate switch 434a-b that is mounted in series between each secondary coil 414a-b' and it's corresponding filament or electrode 436a-b'. By closing the switches 434a-b, the power from each secondary coil 414a-b' is supplied directly to its corresponding filament. In this embodiment, only a single conductor 498' is required to extend between the secondary coils 414a-b'. The capacitor 416' is connected in series along the conductors 498'.

Figure 13:
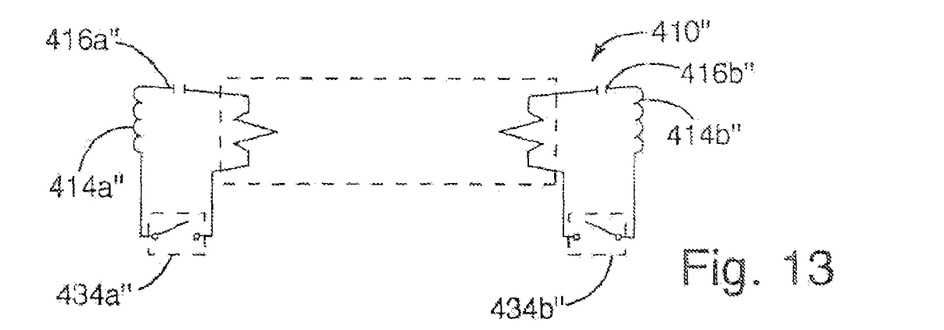
FIG. 13 is a schematic diagram of yet another alternative lamp circuit for the lamp assembly of FIG. 10.

An alternative circuit for a dual-coil lamp assembly 410" is shown in FIG. 13. In this circuit, no conductors are required to extend between the two secondary coils 414a-b'. Instead, each secondary coil 414a-b" includes a dedicated switch 434a-b" and a dedicated capacitor 416a-b". The lamp controller is preferably configured to open and close the two switches 434a-b" in unison. The preferred method for calculating the value of the capacitors 416a-b" is to initially analyze the circuit in accordance with the first disclosed embodiment as though only a single coil and single capacitor were going to be used. The value of the single capacitor of this hypothetical configuration is then halved to provide the value for each of the two capacitors 416a-b" of this embodiment. In some applications, the power may not be evenly distributed between the two secondaries. In such applications, the ratio between the value of the two capacitors should be equivalent to the ratio of the power between the two secondaries.

Figure 14:
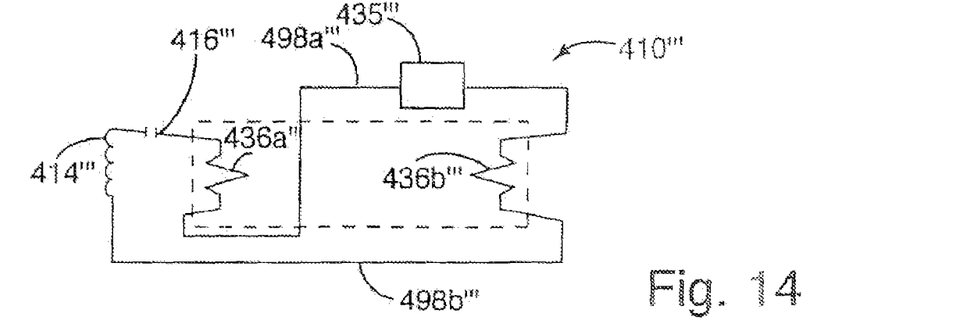
FIG. 14 is a schematic diagram of a further alternative lamp circuit for the lamp assembly of FIG. 10.

Another alternative circuit for a dual-coil lamp 410''' is shown in FIG. 14. In this alternative, only a single secondary coil 414''' is provided. The secondary coil 414''' is connected to electrodes 436a-b''' is provided. This circuit includes a pair of conductors 498a-b''' that extend between the coils. A conventional starter 435''' or other starter mechanism, such as magnetic switches, is included to start the lamp. In this embodiment, the value of the capacitor 416''' is preferably selected in accordance with the method of the first disclosed embodiment.

Figure 15:
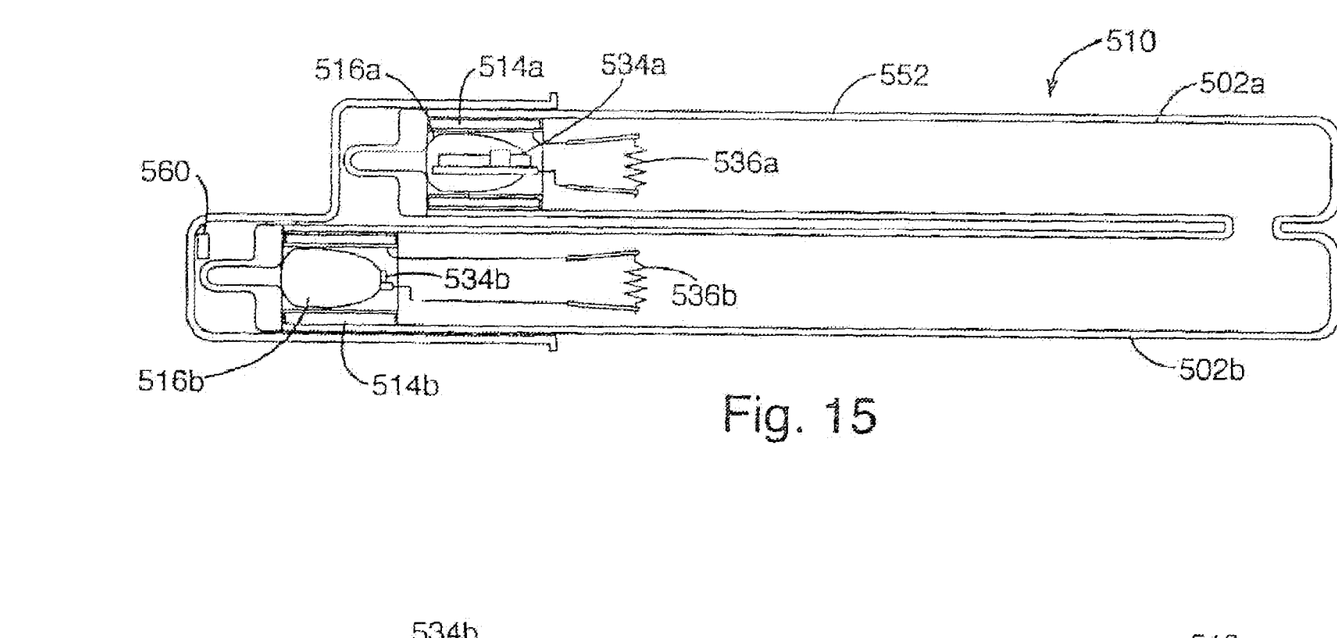
FIG. 15 is a sectional view of an alternative lamp assembly having a PL type fluorescent lamp.
Figure 16:
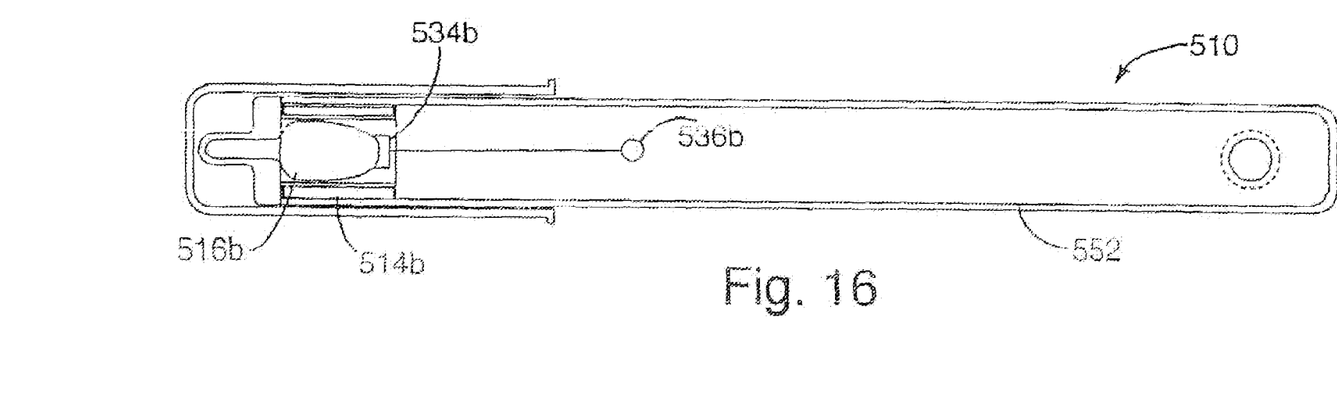
FIG. 16 is a sectional view of the alternative lamp assembly having a PL type fluorescent lamp taken perpendicularly to the sectional view of FIG. 15.

A further alternative embodiment showing the present invention adapted for use in a PL type fluorescent lamp is shown in FIGS. 15 and 16. In this embodiment, the entire lamp circuit is enclosed within the lamp sleeve 552, and no outer sleeve is included. As illustrated, the lamp assembly 510 includes a glass sleeve 552 having to interconnected legs 502a-b. The lamp assembly 510 may include any of the dual coil lamp circuits described above. For purposes of disclosure, this embodiment is described in connection with a lamp assembly 510 having a separate secondary 514a-b mounted in the base of each leg 502a-b. The two secondaries 514a-b are preferably powered by a single primary (not shown) surrounding or adjacent to one end of the lamp assembly 510. Each secondary 514a-b is connected in series with an electrode 536a-b, a capacitor 516a-b and a magnetically actuated starter switch 534a-b. The value of each capacitor 516a-b is selected as described above is connection with the embodiment of FIG. 13. This lamp assembly 510 may also include a sensing magnet 560.

Figure 17:
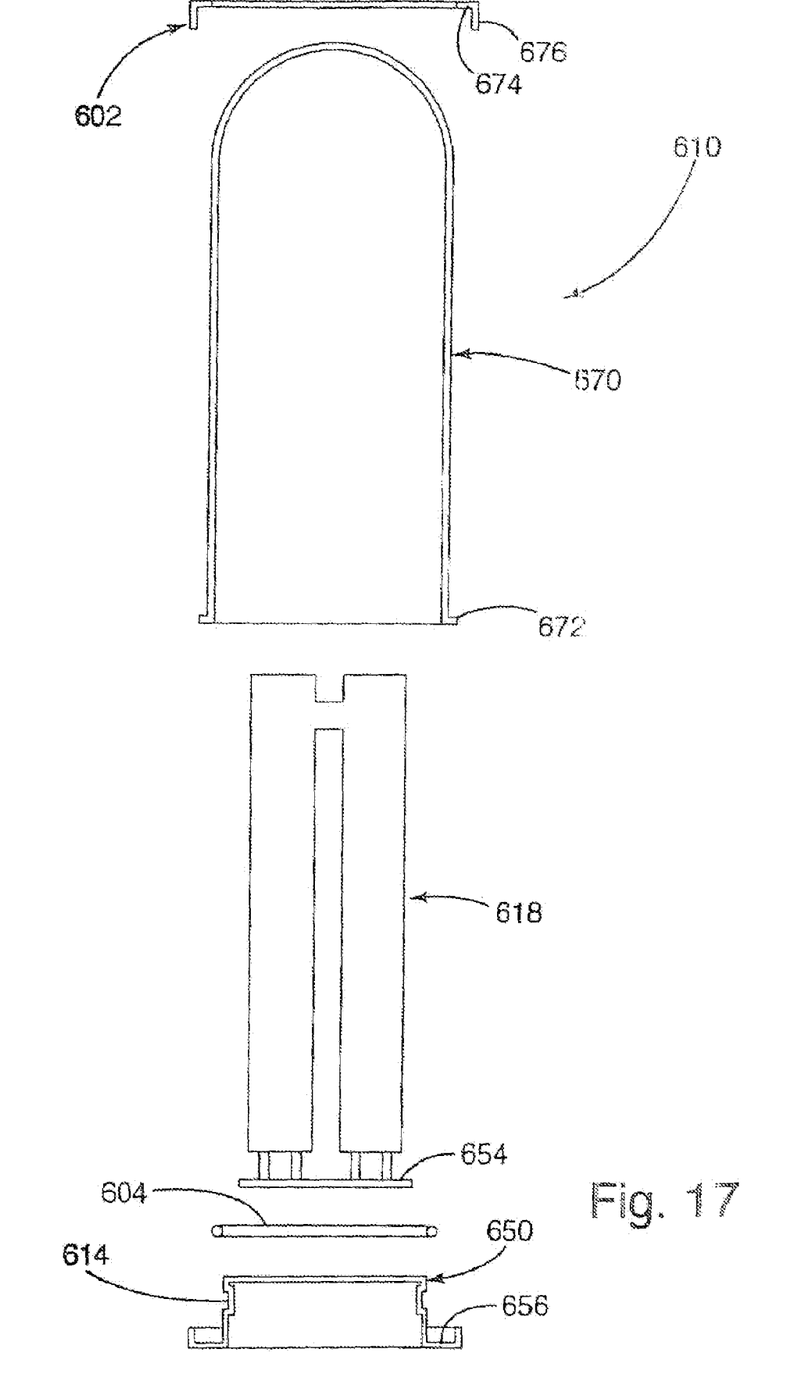
FIG. 17 is a partially sectional exploded view of an alternative lamp assembly.
Figure 18:
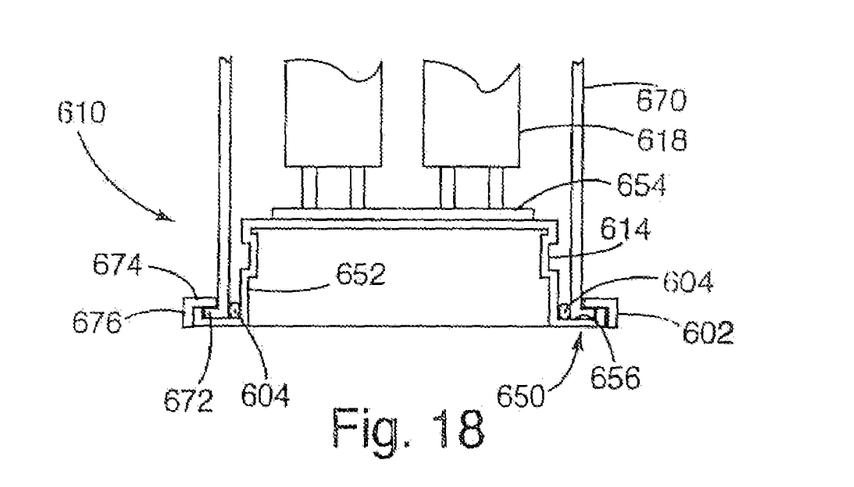
FIG. 18 is a sectional view of a portion of the alternative lamp assembly of FIG. 16.
Figure 19:
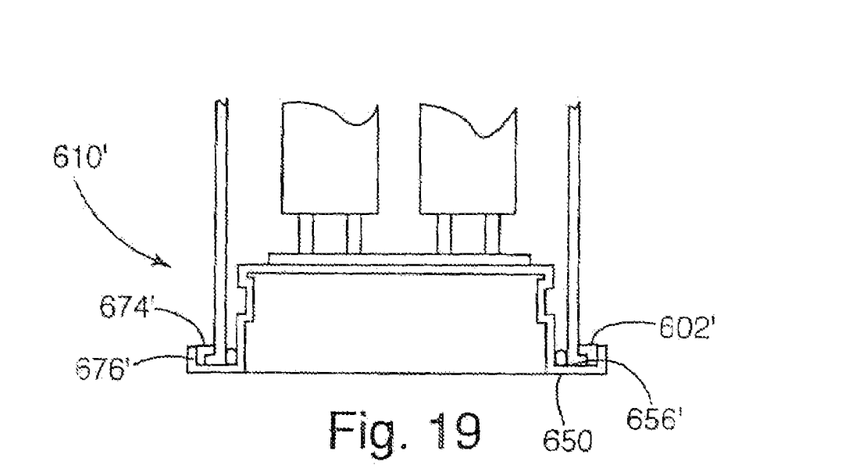
FIG. 19 is a sectional view of a portion of an alternative lamp assembly.
Figure 20:
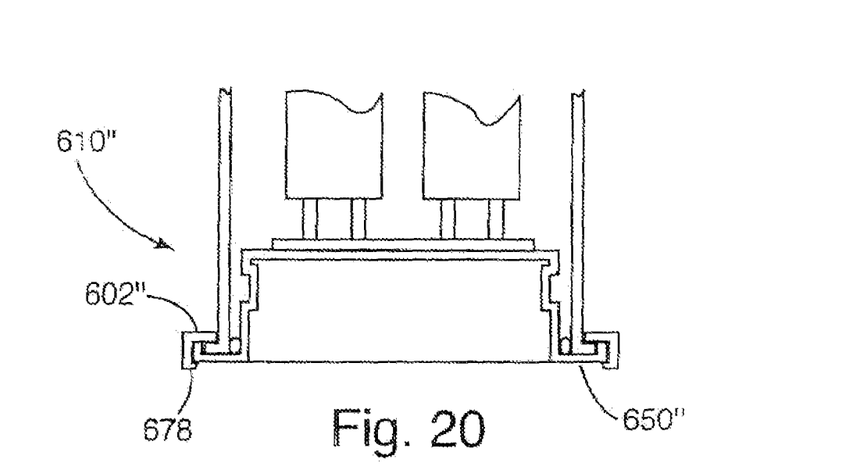
FIG. 20 is a sectional view of a portion of yet another alternative lamp assembly.

An alternative lamp assembly 610 having an alternative sealing structure is shown in FIGS. 17 and 18. As shown in the exploded view of FIG. 17, the lamp assembly 610 generally includes a locking ring 602, an outer sleeve 670, a lamp 618 and a base 650. The locking ring 602, outer sleeve 670 and base 650 cooperate to seal the lamp assembly 610. As perhaps best shown in FIG. 18, the base 650 includes a cylindrical central portion 652 that is shaped to receive the secondary 614 and the lamp 618. More specifically, the lamp 618 is mounted to a printed circuit board assembly ("PCBA") 654, which will preferably also support any capacitor or starter mechanism incorporated into the lamp assembly 610. The lamp/PCBA combination is mounted to the base 650, for example, by fasteners or a snap-fit. The base 650 also includes annular channel 656 that extends around the base 650 to receive the end of the outer sleeve 670. An o-ring 604 is fitted around the central portion 652 within the annular channel 656. The base 650 may include an annular rib (not shown) to prevent the o-ring 604 from riding up the central portion 652. Once assembled, the o-ring 604 is disposed between the inner diameter of the outer sleeve 670 and the outer diameter of the central portion 652 of the base 650. In this position, the o-ring 604 not only provides an effective seal against water, but it also functions as a vibration damper that cushions vibrations between the lamp and the outer sleeve 670. The outer sleeve 670 is a generally cylindrical tube having a closed end and an open end. A bead 672 or other flange extends around the open end of the outer sleeve 670. The outer sleeve 670 is secured to the base 650 by the locking ring 602. The locking ring 602 is generally ring-shaped and is fitted over the outer sleeve 670 and the base 650. The locking ring 602 has a generally inverted L-shaped cross section with a radial leg 674 and an axial leg 676. The radial leg 674 engages the bead 672 and the axial leg 676 engages the outer surface of the base 650. Alternatively, as shown in FIG. 19, the locking ring 602' and base 650' can be configured so that the axial leg 676' is fitted within the annular channel 656'. In either case, the axial leg 676 or 676' is secured to the base 650 or 650' to lock the outer sleeve 670 in the annular channel 656 of the base 650. The locking ring 602 may be attached to the base 650 using various attachment methods. For example, the locking ring 602 may be sonic or heat welded to the base 650. Alternatively, the lamp assembly 610''' may include a locking ring 602" having a lower flange 678 (See FIG. 20) that permits the locking ring 602' to be snap-fitted onto the base 650', or the locking ring and base can includes threads (not shown) to permit the locking ring to be threaded to the base.

The above description is that of various embodiments of the invention. Various alterations and changes can be made without departing from the spirit and broader aspects of the invention as defined in the appended claims, which are to be interpreted in accordance with the principles of patent law including the doctrine of equivalents. Any reference to claim elements in the singular, for example, using the articles □a,□ □an,□ □the□ or □said,□ is not to be construed as limiting the element to the singular.

The invention claimed is:

1. An inductively powered secondary assembly comprising:
   an inductive secondary to receive power from an inductive primary, the inductive secondary having a reactance;
   a load disposed in series with the inductive secondary, the load having an impedance; and
   a capacitor disposed in series with the inductive secondary and the load, the capacitor selected to have a reactance that is substantially equal to or slightly less than the sum of the impedance of the load and the reactance of the inductive secondary, whereby the load and the inductive secondary operate substantially at resonance.

2. The inductively powered secondary assembly of claim 1 wherein said inductive secondary is a coil of LITZ wire.

3. The inductively powered secondary assembly of claim 2 further including a sleeve surrounding and fully enclosing said inductive secondary, said load and said capacitor, said sleeve being unpenetrated.

4. The inductively powered secondary assembly of claim 1 wherein said inductive secondary is a coil of magnetic wire.

5. An inducively powered secondary assembly comprising:
   an inductive secondary to receive power from an inductive primary, the inductive secondary having a reactance;
   a load disposed in series with the inductive secondary, the load having an impedance that is substantially equal to the reactance of the inductive secondary; and
   a capacitor disposed in series with the inductive secondary and the load, the capacitor selected to have a reactance that is substantially equal to or slightly less than the sum of the impedance of the load and the reactance of the inductive secondary, whereby the load and the inductive secondary operate substantially at resonance.

6. The inductively powered secondary assembly of claim 5 wherein said inductive secondary is a coil of LITZ wire.

7. The inductively powered secondary assembly of claim 6 further including a sleeve surrounding and fully enclosing said inductive secondary, said load and said capacitor, said sleeve being unpenetrated.

8. The inductively powered secondary assembly of claim 5 wherein said inductive secondary is a coil of magnetic wire.

* * * * *

UNITED STATES PATENT AND TRADEMARK OFFICE
CERTIFICATE OF CORRECTION

| | | |
|---|---|---|
| PATENT NO. | : 7,474,058 B2 | Page 1 of 1 |
| APPLICATION NO. | : 11/558684 | |
| DATED | : January 6, 2009 | |
| INVENTOR(S) | : David W. Baarman | |

It is certified that error appears in the above-identified patent and that said Letters Patent is hereby corrected as shown below:

On the Title page under (60) Related U.S. Application Data:

"Continuation of application No. 10/977,443, filed on Oct. 29, 2004, now Pat. No. 7,153,178, which is a continuation of application No. 10/455,694, filed on Jun. 5, 2003, now Pat. No. 6,831,417, and a continuation-in-part of application No. 09/592,194, filed on Jun. 12, 2000, now Pat. No. 6,436,299, which is a division of application No. 10/133,860, filed on Apr. 26, 2002, now Pat. No. 6,731,071.

Provisional application No. 60/357,908, filed on Feb. 19, 2002, provisional application No. 60/140,159, filed on Jun. 21,1999, provisional application No. 60/140,090, filed on jun. 21, 1999."

should be --Continuation of application No. 10/977,443, filed on Oct. 29, 2004, now Pat. No. 7,153,178, which is a continuation of application No. 10/455,694, filed on Jun. 5, 2003, now Pat. No. 6,831,417, which is a division of application No. 10/133,860, filed on Apr. 26, 2002, now Pat. No. 6,731,071, which is a continuation-in-part of application No. 09/592,194, filed on Jun. 12, 2000, now Pat. No. 6,436,299.

Provisional application No. 60/357,908, filed on Feb. 19, 2002, provisional application No. 60/140,159, filed on Jun. 21, 1999, provisional application No. 60/140,090, filed on Jun. 21,1999.--

Signed and Sealed this

Eleventh Day of August, 2009

David J. Kappos
*Director of the United States Patent and Trademark Office*